United States Patent [19]

DiFrancesco

[11] 4,349,027
[45] Sep. 14, 1982

[54] NEEDLE GUIDE FOR IMPLANTING INTRA-OCULAR LENS

[76] Inventor: John G. DiFrancesco, Lake Drive South, New Fairfield, Conn. 06810

[21] Appl. No.: 162,013

[22] Filed: Jun. 23, 1980

[51] Int. Cl.³ .............................................. A61B 17/06
[52] U.S. Cl. .................. 128/303 R; 128/340
[58] Field of Search ................. 128/303 R, 339, 340, 128/334 R, 335, 335.5; 223/109 R; 112/227

[56] References Cited

U.S. PATENT DOCUMENTS

| | | | |
|---|---|---|---|
| 755,921 | 3/1904 | O'Neill | 128/334 R |
| 818,152 | 4/1906 | Edwards | 128/339 |
| 3,349,772 | 10/1967 | Rygg | 128/340 |
| 3,470,875 | 10/1969 | Johnson | 3/13 |
| 3,490,455 | 1/1970 | Illig | 128/303 R |
| 3,683,925 | 8/1972 | Frankel | 128/334 C |
| 3,913,148 | 10/1975 | Potthast | 3/13 |
| 4,122,556 | 10/1978 | Poler | 3/13 |
| 4,164,225 | 8/1979 | Johnson et al. | 128/334 R |
| 4,190,049 | 2/1980 | Hager et al. | 128/303 R |
| 4,198,980 | 4/1980 | Clark | 128/303 R |
| 4,214,585 | 7/1980 | Bailey | 128/303 R |

FOREIGN PATENT DOCUMENTS

| | | | |
|---|---|---|---|
| 572263 | 9/1977 | U.S.S.R. | 128/339 |
| 640739 | 1/1979 | U.S.S.R. | 128/339 |

Primary Examiner—Michael H. Thaler
Attorney, Agent, or Firm—Mattern, Ware, Davis and Stoltz

[57] ABSTRACT

A needle guide for intra-ocular surgery designed for insertion through the corneal rim incision to span the anterior chamber of the patient's eye, and being thereby positioned to conduct surgical needles safely past the corneal endothelium, comprises an elongated narrow substantially rectangular guide plate having along each edge an elongated needle flange inturned to form a needle guide chamber dimensioned to embrace a surgical needle during its endwise telescoping passage through the guide chamber, and having an elongated suture-release slot too narrow to permit lateral removal of a surgical needle from the guide chamber, whereby the elongated narrow guide may be inserted spanning an anterior chamber, guided by trans-illumination, a pair of surgical needles secured to opposite ends of a first suture loop interlinked with a retention loop of an intra-ocular lens may be inserted through the respective guide chambers safely passing the endothelium to exit through the sclera opposite the corneal rim incision, leaving the bight of the first suture loop protruding from the incision, the tension maintained on the first suture loop permits the needle guide to be withdrawn through the incision and detached by lateral withdrawal of the first suture loop through the suture release slots, after which the intra-ocular lens may be inserted in the anterior chamber adjacent to the iris and secured by suturing in position spanning the pupil.

6 Claims, 14 Drawing Figures

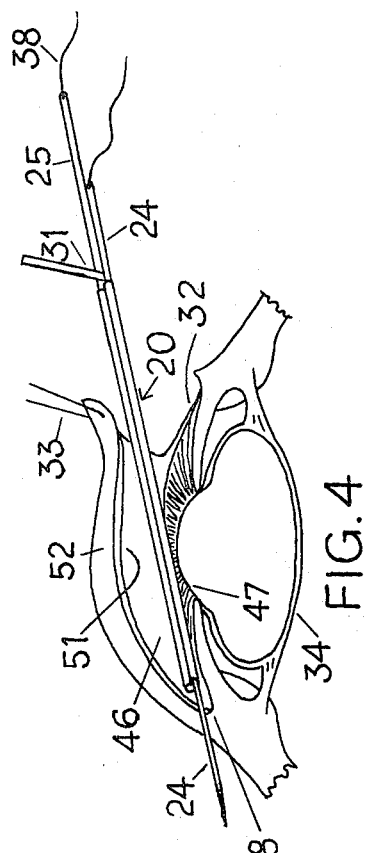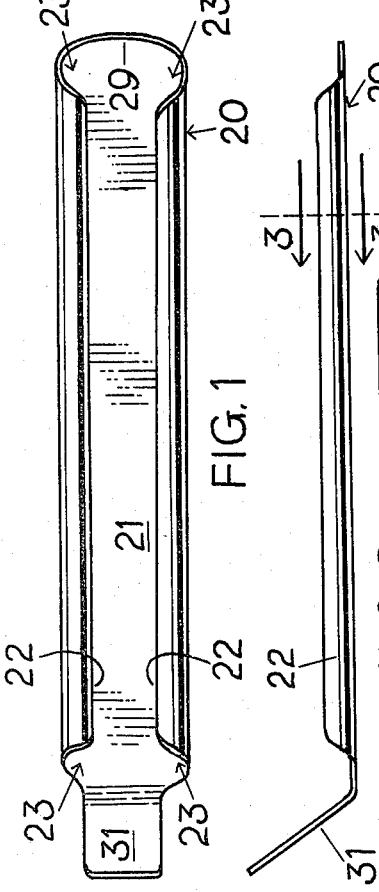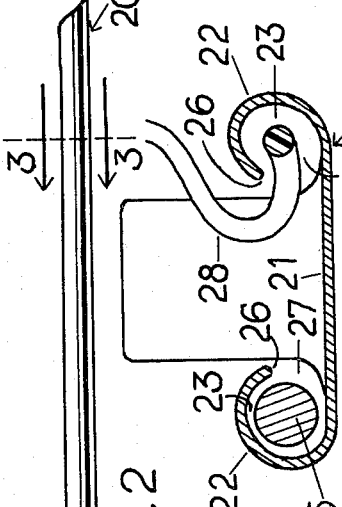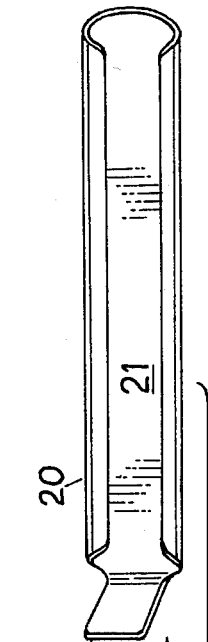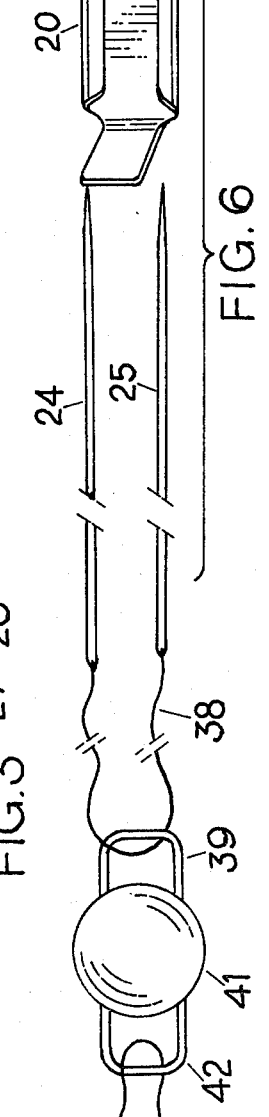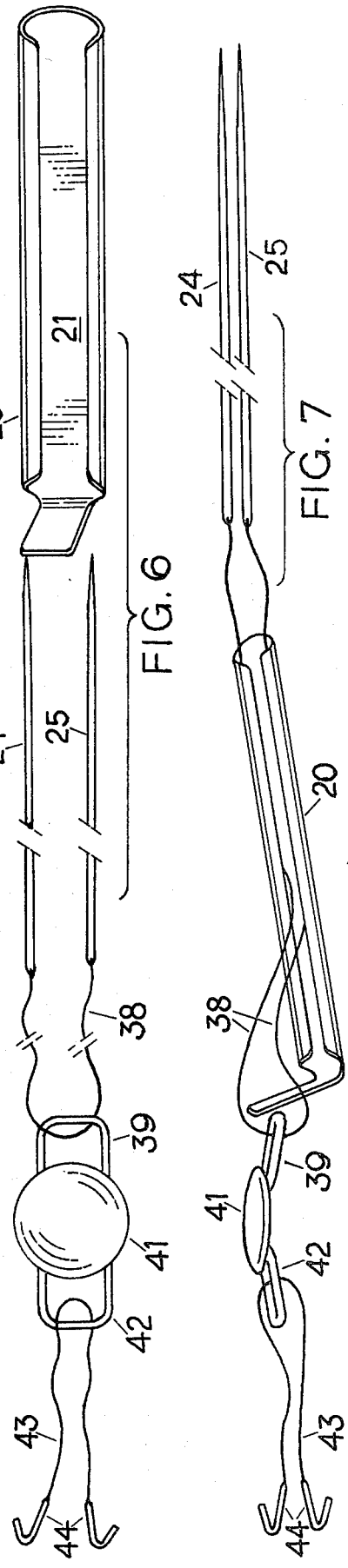

NEEDLE GUIDE FOR IMPLANTING INTRA-OCULAR LENS

TECHNICAL FIELD

This invention relates to methods and apparatus for use in opthalmic surgery and specifically in the implantation of intra-ocular lenses while assuring maximum protection for the delicate eye tissues and particularly the one-celled epthelial layer on the posterior surface of the cornea.

Surgical treatment of cataracts to counteract the light-blocking effects of clouded natural lenses customarily requires the surgical removal of the natural lenses by such means as ultrasonic fragmentation and withdrawal of the natural lens tissue from the patient's eye. The removal of the natural lens requires the substitution of light-focusing optics capable of performing the same lens functions. Glasses designed for this purpose are heavy and clumsy, and suitable contact lenses are often incapable of providing sufficient focusing effect, to substitute for the removed natural lens. From the optical correction standpoint, the most effective substitute lens is an artificial intra-ocular lens actually implanted near the plane of the iris behind the cornea inside the patient's eye. An intra-ocular lens supplies the desired optical correction at the desired plane in the optic system of the eye, producing optimum effect with minimum size, weight and discomfort.

BACKGROUND ART

Numerous patents have described the problems and hazards in intra-ocular lens implants, and have proposed numerous and varied artifical lens structures for this purpose. Examples of these prior art patents are the following:

| | | |
|---|---|---|
| Knight et al | 4,170,661 | 1979 |
| Knight et al | 4,170,043 | 1979 |
| Fedorov et al | 3,673,616 | 1972 |
| Flom | 3,866,249 | 1975 |
| Otter | 3,906,551 | 1975 |
| Potthast | 3,913,148 | 1975 |
| Krasnov | 3,922,728 | 1975 |
| Richards et al | 3,925,825 | 1975 |
| Poler | 4,073,014 | 1978 |
| Poler | 4,080,709 | 1978 |
| Poler | 4,118,808 | 1978 |
| Anis | 4,166,293 | 1979 |
| Schlegel | 4,172,297 | 1979 |
| Welsh | 4,173,798 | 1979 |
| Kelman | 4,174,543 | 1979 |
| Kelman | 4,174,543 | 1979 |
| Kuppinger et al | 4,177,526 | 1979 |

The delicacy of the various eye tissues is easily understood, but the merest touch of the tip of a surgical needle or other surgical instrument on the one-cell layer of the endothelial lining on the posterior face of the cornea is likely to tear some of the cells away from the corneal surface, permanently damaging the eye. The risk of such injury during intra-ocular lens implantation accounts for much of the criticism leveled by consumer advocates and lobbyists against lens implantation surgery. The serious risk of permanent damage to the corneal endothelium, and one particular proposal for minimizing such damage, are described in Knight et al U.S. Pat. No. 4,170,661, in the background paragraphs of that patent. A number of surgical instruments have been proposed to minimize such damage and aid the opthalmic surgeon in lens implantation, in such patents as:

| | | |
|---|---|---|
| Poler | 4,122,556 | 1978 |
| Clark | 4,198,980 | 1980 |
| Hager et al | 4,190,049 | 1980 |

DISCLOSURE OF THE INVENTION

The present invention effectively safeguards the corneal endothelium by bridging the gap across the iris behind the cornea with a single extremely thin flat surgical needle guide, barely thicker than the diameter of a surgical needle. This needle guide may be maneuvered through a corneal rim incision across the iris behind the cornea with the air of trans-illumination supplied from the outside of the cornea.

By the use of this needle guide, two surgical needles may be inserted telescopingly through the guide and through the sclera at the opposite side of the cornea allowing a first suture bight to be inserted extending from the sclera back across the iris toward the corneal rim incision along the opposie edge of the cornea through which the natural lens has already been removed.

By the aid of this suture bight securely positioned in the sclera, the artificial lens with one of its peripheral plastic anchoring loops interlinked with the suture bight may be carefully maneuvered into position near the plane of the iris, with its plastic loops or "clips" spanning the delicate iris tissue, and the first suture bight can then be used to anchor the plastic loop of the intra-ocular lens while an additional surgical suture bight may anchor a corresponding plastic loop at the proximal side of the artificial lens near the corneal's peripheral incision.

The elongated flat rectangular needle guides of the present invention are preferably provided with rolled elongated edges forming hollow needle chambers having open interior-facing slots, too narrow for lateral removal of the surgical needle from the needle chamber, but wide enough to permit the suture filament material to slip through. By this means, the needle guide may be drawn reversely along the slack of the suture bight and disengaged from the suture bight, which remains spanning the iris, amply spaced behind the corneal endothelium.

Accordingly, a principal object of the present invention is to provide methods and apparatus for opthalmic surgeons' use in implantation of artificial intra-ocular lenses.

A further object of the invention is to provide a simple and economical surgical needle guide easily inserted behind the cornea across the iris with no risk to the corneal endothelium.

Still another object of the present invention is to provide needle guides of the above character capable of being retracted from the eye and disengaged from the bight of a surgical filament which has already partially passed in telescoping fashion through the needle guide.

Other objects of the invention will in part be obvious and will in part appear hereinafter.

The invention accordingly comprises the features of construction, combinations of elements, and arrangements of parts which will be exemplified in the constructions hereinafter set forth, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings.

FIG. 1 is a greatly enlarged plan view of a surgical needle guide of the present invention;

FIG. 2 is a corresponding greatly enlarged side elevation view of the needle guide;

FIG. 3 is a still further enlarged cross-sectional elevation view of the needle guide of the present invention, taken along the plane 3—3 shown in FIG. 2;

FIG. 4 is a schematic cross-sectional elevation view of the patient's eye after removal of the natural lens, showing the position of the needle guide of the present invention spanning the iris with a surgical needle shown passing through the needle guide and the sclera of the eye;

FIG. 5 is a corresponding schematic cross-sectional elevation view of the patient's eye after withdrawal of the needle guide and subsequent implantation of an artificial lens in the anterior chamber just forward of the iris and well behind the corneal endothelium;

FIG. 6 is a schematic assembly view showing the needle guide of the invention aligned with a pair of surgical needles suspending between themselves a first surgical suture filament bight interlinked with the plastic loop of an artificial intra-ocular lens whose opposite plastic loop is similarly interlinked with a second suture filament bight, all being positioned prior to insertion of the needle guide spanning the iris of the patient's eye in the position shown in FIG. 4;

FIG. 7 is a schematic assembly view of the components illustrated in FIG. 6, showing the needle guide withdrawn part way along the first surgical suture filament bight, in the process of being disengaged from the suture bight;

BEST MODE FOR CARRYING OUT THE INVENTION

Figure 8:
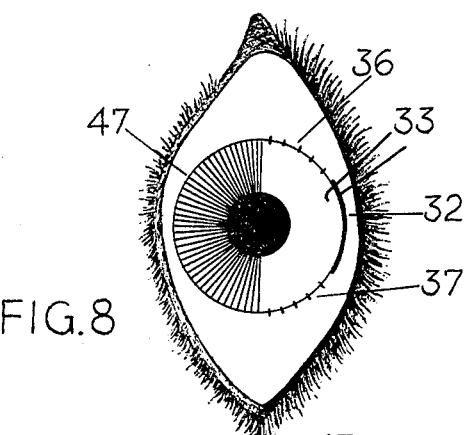
FIGS. 8–14 show successive stages in the implantation of an artificial lens in the anterior chamber of the patient's eye, these all being successive plan views looking directly into the pupil and iris of the patient's eye.

The needle guide 20 characterizing the apparatus of the present invention is a small flat object only slightly thicker than a surgical needle, as shown in FIGS. 1–5. Preferably, the needle guides of the present invention are from two to four millimeters in width. A width of three millimeters has proved highly suitable. The elongated needle guide 20 is designed to extend lengthwise across the width of the iris inside the cornea and to protrude therefrom through the corneal rim incision as indicated in FIG. 4. The average internal diameter of adults' corneal rims is about twelve millimeters, and a length of twenty millimeters for the needle guide 20 of the present invention has proved entirely satisfactory.

As shown in FIGS. 1 and 2, the needle guide 20 comprises a substantially rectangular elongated narrow guide plate 21 preferable formed of thin sheet stainless steel. Each of the elongated edges of guide plate 21 is rolled upward and inward to form an inturned rolled needle flange 22 enclosing a hollow cylindrical needle guide chamber 23. As shown in FIG. 3, chamber 23 is dimensioned to embrace a surgical needle 24 which may be inserted therein and moved telescopingly therethrough in endwise translation movement, entering the proximal end of the needle guide chamber 23 and exiting from the distal end 29. Each flange 22 is provided with an elongated rim 26 spaced away from the guide plate 21 and providing an elongated suture release slot 27 therebetween, as shown in FIG. 3.

Each slot 27 is wide enough to permit normal surgical sutures to pass therethrough. "10-0" sutures are 0.024 millimeters in diameter and "9-0" sutures are 0.032 millimeters in diameter. A suture release slot width of 0.050 millimeters thus permits the withdrawal of these standard suture filaments through the suture release slots. Surgical needle diameters for opthalmic surgery normally range from 0.203 millimeters to 0.432 millimeters in outside diameter, and therefore an interior diameter of 0.500 millimeters for chamber 23 provides ample sliding clearance for endwise translation or telescoping movement of the standard surgical needles through and out of the needle chambers 23 enclosed within rolled needle flanges 22.

As indicated in FIG. 3, the significant limitation on the relative sizes of the needle chamber 23 and the suture release slot 27 is the selective retention of the surgical needle inside this needle chamber 23 while the much finer suture filament 28 is not retained and is free for lateral withdrawal through the slot 27. The forward distal end of the needle guide 20 is preferably formed as a smooth rounded curved distal tip 29, blending smoothly with the forward ends of the needle flanges 22 to form a blunt rounded and smoothly curved distal tip for insertion across the anterior chamber into contact with the internal angle surface of the sclera, at the junction of iris and cornea, as shown in FIG. 4 and FIGS. 9–11.

The opposite or proximal end of the needle guide 20 is preferably formed with an upturned retraction flange 31 extending angularly upward at an acute angle, which may be approximately 60°, for example, from the plane of the guide plate 21. Retraction flange 31 is narrow enough to avoid blocking the proximal entrance ends of needle chambers 23, as indicated in FIG. 4, and extends upward between the needle chambers to provide a gripping flange which may be seized between forcep tips and utilized for maneuvering the needle guide 20 into the corneal rim incision and across the anterior chamber in the position shown in FIG. 4.

Intra-Ocular Lens Implantation Suture Assembly

FIGS. 6 and 7 show the assembly of the artificial intra-ocular lens, the sutures, the surgical needles and the needle guide 20 employed in performing surgical procedures in accordance with the present invention, in the fashion illustrated in FIGS. 4 and 5. These surgical procedures can be explained in greater detail by reference to the successive schematic plan views of FIGS. 8–14.

As indicated in FIGS. 5 and 8, the cataract "section" procedure for removal of the natural lens by ultrasonic fragmentation, for example, is performed through a corneal rim incision 32, with the corneal rim immediately overlying the rim incision being raised by a suture 33 to maintain a needed opening for this procedure. The hyloid membrane 34 is left in position behind the space previously occupied by the natural lens, thus maintaining the vitreous humor intact within the eyeball. The aqueous humor removed from the anterior chamber of the eye is replaced by an air bubble, with a film of aqueous humor fluid spanning the corneal rim incision 32.

Following the removal of the natural lens, the roughly semi-circular corneal rim incision is partially sutured from each side with sutures 36 and 37 (FIG. 8) leaving an opening about five millimeters wide at the "12 o'clock" topmost position in the corneal rim, through which the insertion of the artificial intra-ocular lens is accomplished.

The assembly of the components ilustrated in FIGS. 6 and 7 is prepared for use during the lens implantation, including a needle guide 20, a pair of surgical needles 24 and 25 suspending between themselves a first suture loop 38 interlinked with a distal or inferior retention loop 39 of an intra-ocular lens 41, whose proximal or superior loop 42 is itself interlinked with a second fixation suture loop 43, incorporating suitable terminal suture hooks 44.

Figure 9:
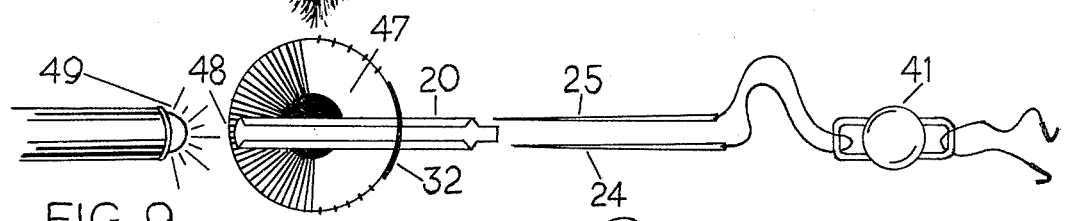
Figure 10:
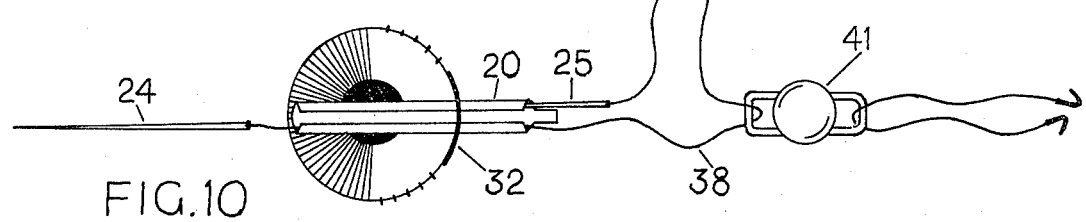

As indicated in FIG. 4 and FIG. 9, the first step in the implantation procedure is the insertion of the needle guide 20 through corneal rim incision 32 across the anterior chamber 46 in front of iris 47, bringing the distal tip 29 of the guide 20 into contact with the sclera 48 at the angle, the base of the iris, preferably guided by transillumination through the cornea from a light source 49 positioned outside the cornea opposite the corneal rim incision 32, as indicated in FIG. 9.

The needle guide 20 spanning the anterior chamber 46 minimizes the risk of contact with or other injury to the corneal endothelium 51 on the posterior surface of the cornea 52 which remains arched above the anterior chamber in the manner shown in FIGS. 4 and 5 during this procedure. One of the surgical needles 24 is next inserted through a chamber 23 of the needle guide 20 from the position shown in FIG. 9 through the position shown in FIG. 4 to the position shown in FIG. 10, drawing one end of the first suture loop 38 into the needle guide, with the surgical needle 24 passing through the sclera 48 as indicated in FIG. 4, and being drawn out to the outside of the eyeball.

The second needle 25 is then inserted into the second needle chamber 23 in the guide 20, repeating the same operation, extending needle 25 through chamber 23 in guide 20 through the sclera 48 and out to the outside of the eyeball, drawing the other side of first suture loop 38 into needle guide 20.

Figure 11:
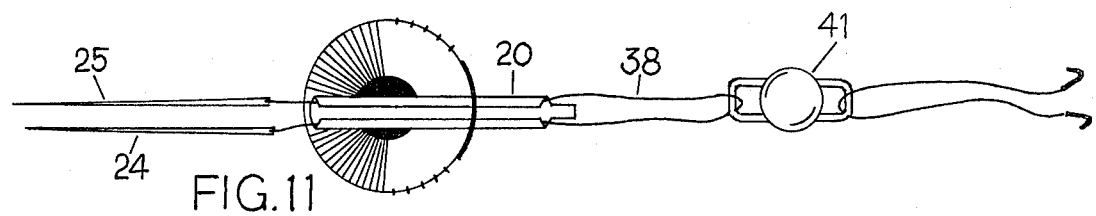
Figure 12:
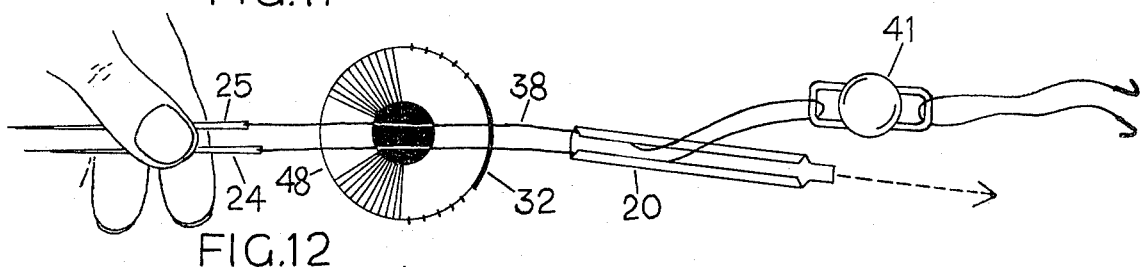

Holding the two needles 24 and 25 outside the sclera 48, as indicated in FIG. 12, the needle guide may then be withdrawn out along the two parallel sides of suture filament 38, from the position shown in FIG. 11 to the position shown in FIG. 12, outside the corneal rim incision 32. There, the suture guide 20 may be maneuvered to disengage its needle chambers 23 from suture filament 38 through the suture release slots 27, in the manner that the filament 28 is shown being maneuvered through filament release slot 27 in FIG. 3, FIGS. 7 and 12 show needle guide 20 in the process of disengagement from the suture filament 38.

Figure 13:
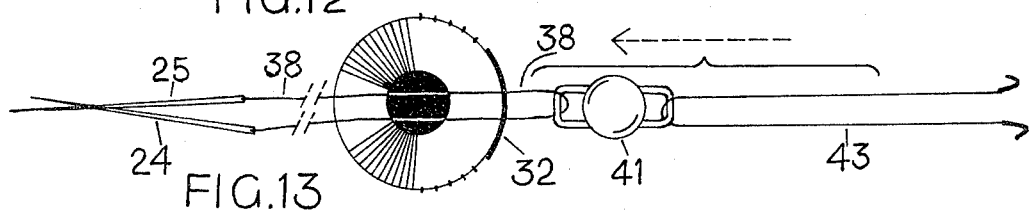

The artificial intra-ocular lens is then inserted through corneal rim incision 32, being guided by the first suture loop 38 maintained under tension if desired, thereby assuring that the lens 41 remains close to the iris 47 and well away from the corneal endothelium 51. As indicated in FIG. 13, the first suture loop 38 and the second fixation suture loop 43 may be stretched apart in tension to suspend the artificial lens 41 therebetween, during this maneuvering insertion into the anterior chamber, or alternatively forceps or similar instruments may be used for more positive positioning of the artificial lens 41.

Figure 14:
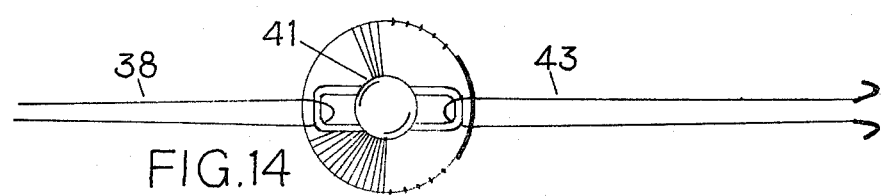

The sutures 38 and 43 are normally secured through the sclera to stabilize and fix the position of the artificial lens 41 in the anterior chamber 46 in alignment with the iris 47, in the implanted position illustrated in FIGS. 5 and 14. The sutures 38 and 43 are tied in this position leaving the loops 39 and 42 of the artificial lens 41 firmly anchored at the juncture of the sclera with the angle meshwork near the ciliary body at the base of the iris.

The foregoing procedure minimizes the risk of contact with the endothelial cells on the posterior side of the cornea, and also minimizes damage to the delicate iris 47, which remains free to respond in the normal way to changes in external light intensity in order to vary the size of the pupil.

The lens implantation procedure is completed by tensing the eye with saline solution, replacing the bubble of air previously suporting the cornea 52 and maintained in position across the corneal rim incision 32 by a film of the aqueous humor from inside the anterior chamber 46. The saline solution will be replaced by fresh aqueous humor secreted by the ciliary body in the eye in a short time, and additional sutures are applied to close the corneal rim incision 32 and to secure it against any leakage of this aqueous humor from the anterior chamber 46.

Variations in the shape of needle guide 20 may be utilized to change its length or width, but its generally rectangular overall shape, thinness and narrowness make it a highly efficient surgical tool for performing the functions of guiding the surgical needles 24 and 25 across the anterior chamber without risk of injury to the iris 47 or to the endothelial cells 51, simplifying the lens implantation procedure and minimizing risk of injury to the eye, and thereby helping to assure the success of the intra-ocular lens implant procedure.

It will thus be seen that the objects set forth above, among those made apparent from the preceding description, are efficiently attained and, since certain changes may be made in the above constructions without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

I claim:

1. A needle guide for intra-ocular surgery to fixate an intra-ocular lens following cataract removal, designed for insertion through a corneal-rim incision into a temporary position spanning the anterior chamber and being thereby positioned to conduct straight surgical needles safely across the anterior chamber and past the corneal endothelium, comprising an elongated thin narrow substantially flat and rectangular unitary guide plate having an elongated needle flange inturned and downturned along each elongated edge of the guide plate to form a cylindrical needle guide chamber of substantially uniform cross section dimensioned to embrace a straight surgical needle during its endwise telescoping passage into, through and beyond the guide chamber, each flange having an elongated rim spaced away from the guide plate to provide an elongated inwardly-opening suture-release slot of substantially uniform width therebetween, each slot being too narrow to permit lateral removal of a surgical needle from the guide chamber, whereby the elongated narrow guide may be inserted spanning the anterior chamber, guided by trans-illumination, a pair of surgical needles secured to opposite ends of a first suture loop and forming a double armed suture interlinked with a retention loop of an intra-ocular lens may be inserted into and moved through the respective guide chambers safely passing the endothelium to exit through the sclera opposite the corneal rim incision, leaving the bight of the first suture loop protruding from the incision, and tension maintained on the first suture loop permits the needle guide to be withdrawn through the incision and detached from the first suture loop by lateral withdrawal of the first suture loop through the suture-release slots, after which the intra-ocular lens may be inserted adjacent to the iris and secured by suturing in position spanning the pupil.

2. The elongated needle guide defined in claim 1 having a smoothly rounded curved distal end.

3. The elongated needle guide defined in claim 1 having an upstanding retraction flange protruding from its proximal end in a direction transverse to the guide plate.

4. The needle guide defined in claim 1, wherein each needle guide chamber has an internal diameter greater than 0.500 millimeters.

5. The needle guide defined in claim 1, wherein each suture-release slot is wider than 0.060 millimeters and is narrower than 0.200 millimeters, retaining surgical needles while permitting lateral withdrawal of surgical sutures.

6. The needle guide defined in claim 1, formed of thin sheet stainless steel.

* * * * *